US006299620B1

(12) United States Patent
Shadduck et al.

(10) Patent No.: US 6,299,620 B1
(45) Date of Patent: Oct. 9, 2001

(54) INSTRUMENTS AND TECHNIQUES FOR INDUCING NEOCOLLAGENESIS IN SKIN TREATMENTS

(75) Inventors: John H. Shadduck, Tiburon; James A. Baker, Palo Alto, both of CA (US)

(73) Assignee: AQ Technologies, Inc., Tiburon, CA (US)

( * ) Notice: Subject to any disclaimer, the term of this patent is extended or adjusted under 35 U.S.C. 154(b) by 0 days.

(21) Appl. No.: 09/475,480

(22) Filed: Dec. 30, 1999

(51) Int. Cl.$^7$ ..................................... A61M 1/00
(52) U.S. Cl. ........................... 606/131; 604/289
(58) Field of Search ................... 606/131, 132, 606/159; 604/289, 290, 313, 315

(56) References Cited

U.S. PATENT DOCUMENTS

| | | | |
|---|---|---|---|
| 2,608,032 | 8/1952 | Garver | 51/11 |
| 2,921,585 | 1/1960 | Schumann | 128/355 |
| 3,085,573 | 4/1963 | Meyer et al. | 128/240 |
| 3,476,112 | 11/1969 | Elstein | 128/305 |
| 3,574,239 | 4/1971 | Sollerud | 4/1 |
| 3,715,838 | 2/1973 | Young et al. | 51/12 |
| 4,182,329 | 1/1980 | Smit et al. | 128/256 |
| 4,216,233 | 8/1980 | Stein | 424/350 |
| 4,560,373 | 12/1985 | Sugino et al. | 604/30 |
| 4,646,480 | 3/1987 | Williams | 51/424 |
| 4,676,749 | 6/1987 | Mabille | 433/88 |
| 4,706,676 | 11/1987 | Peck | 128/632 |
| 4,754,756 | * 7/1988 | Shelanski | 606/131 |
| 4,757,814 | 7/1988 | Wang et al. | 128/318 |
| 4,900,316 | 2/1990 | Yamamoto | 604/313 |

(List continued on next page.)

FOREIGN PATENT DOCUMENTS

| | | |
|---|---|---|
| 34 21 390 | 12/1985 | (DE) . |
| 234 608 | 4/1986 | (DE) . |
| 258 901 | 3/1988 | (EP) . |
| 553076 | 12/1956 | (IT) . |
| 1184922 | 10/1987 | (IT) . |

*Primary Examiner*—Gene Mancene
*Assistant Examiner*—Michael B. Priddy
(74) *Attorney, Agent, or Firm*—James F. Hann; Haynes, Beffel & Wolfeld LLP

(57) ABSTRACT

A system for atraumatic removal of skin surface layers in a treatment to induce neocollagenesis in the dermis to reduce wrinkles and alter the architecture of the dermal layers. A preferred embodiment of the inventive system comprises (i) a hand-held instrument with a resilient working skin interface that carries microscopic diamond fragments for abrading the skin surface in a controlled manner; (ii) a fluid source for supplying sterile fluids to the skin interface for cleaning skin debris from the skin interface; and (iii) a negative pressure source for pulling fluid to the skin interface and thereafter aspirating fluid and skin debris from a treatment site. The skin interface is formed of a resilient material such as silicone to allow the working end to flex and atraumatically engage the skin surface as it is translated across a treatment site. The system also carries a disposable cartridge filled with fluid in the hand-held instrument. The method of the invention includes: (i) actuating a negative pressurization source communicating with the skin interface via a plurality of apertures therein to draw the skin into the concave abrasive architecture of the working end; (ii) translating the abrasive architecture across the treatment site to cut or abrade a skin surface layer; and (iii) contemporaneous with the cutting step, flowing a fluid (e.g., sterile water) generally about and across the abrasive architecture between an arrangement of inflow and outflow apertures to remove skin debris and hydrate the skin.

38 Claims, 11 Drawing Sheets

U.S. PATENT DOCUMENTS

| | | | | |
|---|---|---|---|---|
| 4,917,086 | * | 4/1990 | Feltovich et al. | 606/132 |
| 5,037,432 | | 8/1991 | Molinari | 606/131 |
| 5,100,412 | * | 3/1992 | Rosso | 606/131 |
| 5,207,234 | | 5/1993 | Rosso | 128/898 |
| 5,810,842 | * | 9/1998 | Di Fiore et al. | 606/131 |
| 5,873,881 | * | 2/1999 | McEwen et al. | 606/132 |
| 5,971,199 | * | 10/1999 | Naldoni | 606/131 |
| 5,971,999 | | 10/1999 | Naldoni | 606/131 |
| 6,024,733 | | 2/2000 | Eggers et al. | 604/500 |
| 6,039,745 | * | 3/2000 | Di Fiore et al. | 606/131 |
| 6,080,165 | * | 6/2000 | DeJacma | 606/131 |
| 6,080,166 | * | 6/2000 | McEwen et al. | 606/132 |
| 6,136,008 | * | 10/2000 | Becker et al. | 606/131 |
| 6,139,553 | * | 10/2000 | Dotan | 606/131 |
| 6,139,554 | * | 10/2000 | Karkar et al. | 606/131 |
| 6,162,232 | * | 12/2000 | Shadduck | 606/131 |

* cited by examiner

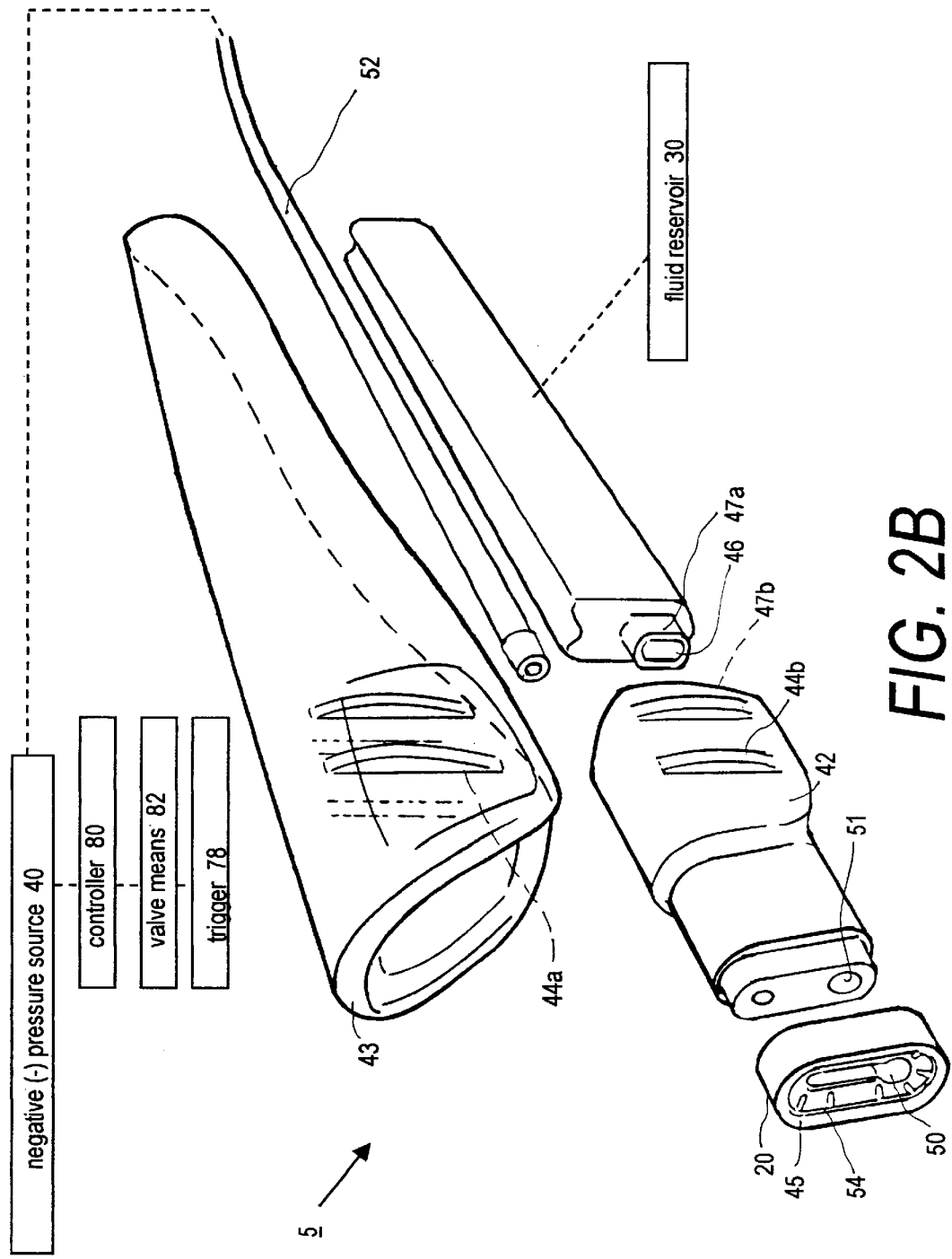

INSTRUMENTS AND TECHNIQUES FOR INDUCING NEOCOLLAGENESIS IN SKIN TREATMENTS

BACKGROUND OF THE INVENTION

1. Field of the Invention

The present invention relates to devices for dermatology and more particularly to a skin resurfacing system that utilizes (i) a skin interface having a diamond fragment abrading surface for removing skin surface layers as the working end is translated over a patient's skin, (ii) a source for delivery of a sterile fluids to the skin interface of the system; and (iii) an aspiration system for delivering fluids to and removing fluids and skin debris from the treatment site.

2. Description of Background Art

Dermatologists and plastic surgeons have used various methods for removing superficial skin layers to cause the growth of new skin layers (i.e., commonly described as skin resurfacing techniques) since the early 1900's. Early skin resurfacing treatments used an acid such as phenol to etch away surface layers of a patient's skin that exhibited damage which thereafter were replaced by new skin. (The term damage when referring to a skin disorder is herein defined as any cutaneous defect, e.g., including but not limited to rhytides, hyperpigmentations, acne scars, solar elastosis, other dyschromias, stria distensae, serborrheic dermatitus).

Following the removal of surface skin layers at a particular depth, no matter the method of skin removal, the body's natural wound-healing response begins to regenerate the epidermis and underlying wounded skin layers. The new skin layer will then cytologically and architecturally resemble a younger and more normal skin. The range of resurfacing treatments can be divided generally into three categories based on the depth of the skin removal and wound: (i) superficial exfoliations or peels extending into the epidermis, (ii) medium-depth resurfacing treatments extending into the papillary dermis; and (iii) deep resurfacing treatments that remove tissue to the depth of the reticular dermis (see FIGS. 1A–1B).

Modern techniques for skin layer removal include: $CO_2$ laser resurfacing which falls into the category of a deep resurfacing treatment; Erbium laser resurfacing which generally is considered a medium-depth treatment; mechanical dermabrasion using high-speed abrasive wheels which results in a medium-depth or deep resurfacing treatment; and chemical peels which may range from a superficial to a deep resurfacing treatment, depending on the treatment parameters. A recent treatment, generally called micro-dermabrasion, has been developed that uses an air-pressure source to deliver abrasive particles directly against a patient's skin at high-velocities to abrade away skin layers. Such a micro-dermabrasion modality may be likened to sand-blasting albeit at velocities that do not cause excessive pain and discomfort to the patient. Micro-dermabrasion as currently practiced falls into the category of a superficial resurfacing treatment.

A superficial exfoliation, peel or abrasion removes some or all of the epidermis (see FIGS. 1A–1B) and thus is suited for treating very light rhytides. Such a superficial exfoliation is not effective in treating many forms of damage to skin. A medium-depth resurfacing treatment that extends into the papillary dermis (see FIG. 1B) can treat many types of damage to skin. Deep resurfacing treatments, such as $CO_2$ laser treatments, that extend well into the reticular dermis (see FIG. 1B) cause the most significant growth of new skin layers but carry the risk of scarring unless carefully controlled.

It is useful to briefly explain the body's mechanism of actually resurfacing skin in response to the removal of a significant depth of dermal layers. Each of the above-listed depths of treatment disrupts the epidermal barrier, or a deeper dermal barrier (papillary or reticular), which initiates varied levels of the body's wound-healing response. A superficial skin layer removal typically causes a limited wound-healing response, including a transient inflammatory response and limited collagen synthesis within the dermis. In a medium-depth or a deep treatment, the initial inflammatory stage leads to hemostasis through an activated coagulation cascade. Chemotactic factors and fibrin lysis products cause neutrophils and monocytes to appear at the site of the wound. The neutrophils sterilize the wound site and the monocytes convert to macrophages and elaborate growth factors which initiate the next phase of the body's wound-healing response involving granular tissue formation. In this phase, fibroblasts generate a new extracellular matrix, particularly in the papillary and reticular dermis, which is sustained by angiogenesis and protected anteriorly by the reforming epithelial layer. The new extracellular matrix is largely composed of collagen fibers (particularly Types I and III) which are laid down in compact parallel arrays (see FIG. 1B). It is largely the collagen fibers that provide the structural integrity of the new skin—and contribute to the appearance of youthful skin.

All of the prevalent types of skin damage (rhytides, solar elastosis effects, hyperpigmentation, acne scars, dyschromias, melasma, stria distensae) manifest common histologic and ultrastructural characteristics, which in particular include disorganized and thinner collagen aggregates, abnormalities in elastic fibers, and abnormal fibroblasts, melanocytes and keratinocytes that disrupt the normal architecture of the dermal layers. It is well recognized that there will be a clinical improvement in the condition and appearance of a patient's skin when a more normal architecture is regenerated by the body's wound-healing response. Of more significance to a clinical improvement is skin is the creation of more dense parallel collagen aggregates with decreased periodicity (spacing between fibrils). The body's wound-healing response is responsible for synthesis of these collagen aggregates. In addition to the body's natural wound healing response, adjunct pharmaceutical treatments that are administered concurrent with, or following, a skin exfoliations can enhance the development of collagen aggregate to provide a more normal architecture in the skin—the result being a more youthful appearing skin.

The deeper skin resurfacing treatments, such as laser ablation, peels and mechanical dermabrasion have drawbacks. The treatments are best used for treatments of a patient's face and may not be suited for treating other portions of a patient's body. For example, laser resurfacing of a patient's neck or décolletage may result in post-treatment pigmentation disorders. All the deep resurfacing treatments are expensive, require anesthetics, and must be performed in a clinical setting. The most significant disadvantage associated with deep resurfacing treatments relates to the post-treatment recovery period. It may require up to several weeks or even months to fully recover and to allow the skin the form a new epidermal layer. During a period ranging from a few weeks to several weeks after a deep resurfacing treatment, the patient typically must wear heavy make-up to cover redness thus making the treatment acceptable only to women.

The superficial treatment offered by micro-dermabrasion has the advantage of being performed without anesthetics and requiring no extended post-treatment recovery period.

However, micro-dermabrasion as currently practices also has several disadvantages. First, a micro-dermabrasion treatment is adapted only for a superficial exfoliation of a patient's epidermis which does not treat many forms of damage to skin. Further, the current micro-dermabrasion devices cause abrasive effects in a focused area of the skin that is very small, for example a few mm$^2$, since all current devices use a single pin-hole orifice that jets air and abrasives to strike the skin in a highly focused area. Such a focused treatment area is suitable for superficial exfoliations when the working end of the device is passed over the skin in overlapping paths. Further, such focused energy delivery is not well suited for deeper skin removal where repeated passes may be necessary. Still further, current micro-dermabrasion devices are not suited for deeper skin removal due to the pain associated with deep abrasions. Other disadvantages of the current micro-dermabrasion devices relate to the aluminum oxide abrasive particles that are typically used. Aluminum oxide can contaminate the working environment and create a health hazard for operators and patients alike. Inhalation of aluminum oxide particles over time can result in serious respiratory disorders.

SUMMARY OF THE INVENTION

The present invention comprises a hand-held instrument adapted for pain-free removal of skin layers in a treatment to induce neocollagenesis in the dermis to reduce wrinkles and alter the architecture of the dermal layers. A preferred embodiment of the inventive system comprises (i) a hand-held instrument with a resilient working skin interface that carriers microscopic diamond fragments for abrading the skin surface in a controlled manner, (ii) a fluid source for supplying sterile fluids to the skin interface for cleaning skin debris from the skin interface; and (iii) a negative (–) pressure source for pulling fluid to the skin interface and thereafter aspirating fluid and skin debris from a treatment site.

More in particular, the working end that carries the resilient skin interface and sharp-edged diamond fragments is detachable from an intermediate instrument body and is inexpensive and disposable after being used for a single treatment. A preferred embodiment of hand-held instruments has a cartridge-type fluid reservoir that is detachable from the intermediate body section and is disposable. The working end defines a skin interface that engages and cuts or abrades the skin as it is translated across a treatment site. A preferred working end has a central channel and outflow aperture that communicates with a remote negative pressure source via a flexible tube. The skin interface is configured with a plurality of fluid inflow apertures generally about a perimeter of the skin interface. Preferably, the inflow apertures are located within a groove structure that allows substantial volume of fluid to be carried within the grooves and in contact with the treatment site. Intermediate to the arrangement of inflow and outflow apertures is a major portion of the skin interface that carries the diamond fragments, which range in diameter from about 10 $\mu$m to about 250 $\mu$m.

Of particular interest, the skin surface is formed of a resilient material such as silicone to allow the working end to flex and atraumatically engage the skin surface as it is translated across a treatment site. Also of particular interest, the suspension of the diamond fragments in resilient silicone seems to allow a slight movement or adjustment of the diamond fragments as the diamond abrasive architecture is translated over skin. In other words, the diamond fragments float to a some extent as they cut the skin surface and patients report that skin layer removals to a significant depth can be accomplished substantially without pain.

The aspiration source of the inventive system has multiple functions: (i) to draw the skin surface into a concave form of the skin interface and the diamond cutting architecture to perform the method of removing skin surface layers; (ii) to draw a sterile fluid across the diamond architecture to remove skin debris from the skin interface; and (iii) to further aspirate the skin debris and spent fluid volume to a remote collection reservoir.

In practicing a method of the invention, the following steps are performed, the system operator (i) places the skin interface carrying the abrasive architecture against the patient's skin in a treatment site; (ii) actuates a negative pressurization source in fluid communication an arrangement of apertures in the skin interface to draw the skin into a concavity of the skin interface and against the abrasive architecture; (iii) translates the abrasive architecture across the treatment site to cut or abrade a skin surface layer; and (iv) contemporaneous with the cutting step, flowing a fluid (e.g., sterile water) generally about and across the abrasive architecture between the arrangement of inflow and outflow apertures in the skin interface under the negative pressures forces to (A) remove the skin debris and clean abrasive architecture; (B) to hydrate the skin to facilitate surface layer cutting, and (C) to cool the skin to make the skin treatment more pain-free.

In general, the invention provides a system and techniques for removing skin surface layers in a controlled manner.

The invention advantageously provides a technique to induce neocollagenesis in a patient's skin.

The invention advantageously provides a technique and system for rejuvenating a patient's skin by surface layer removal to thereby induce the body's wound healing response to cause neocollagenesis in the dermis of the treatment area.

The invention provides a system with a resilient skin interface that carries exposed sharp-edged diamond fragments for controlled cutting or abrasion of the skin surface.

The invention advantageously provides a system with a resilient skin interface that flexes to conform to the skin surface as it is translated across a skin treatment site.

The invention provides a working end in which sharp-edged diamond fragments are resiliently suspended in a flexible silicone.

The invention advantageously provides a fluid source for supplying a fluid to a perimeter of the skin interface to cool the skin, hydrate the skin and remove skin debris from the skin interface during use.

The invention advantageously provides an aspiration source communicating with a central aperture in the skin interface for drawing fluid across the skin interface to remove skin debris and aspirate such skin debris to a remote collection source.

The invention advantageously provides an instrument handle with a cartridge-type fluid reservoir that is removable and disposable.

The invention advantageously provides an injection-molded working end that carries diamond fragments that is inexpensive and disposable.

Other objects and advantages of the invention will be apparent from the following description, the accompanying drawings and the appended claims. Additional advantages and features of the invention appear in the following description in which several embodiments are set forth.

BRIEF DESCRIPTION OF THE DRAWINGS

FIG. 2B is an exploded perspective view of components of the exemplary body and working end of FIG. 2A.

DETAILED DESCRIPTION OF THE INVENTION

Figure 1A:
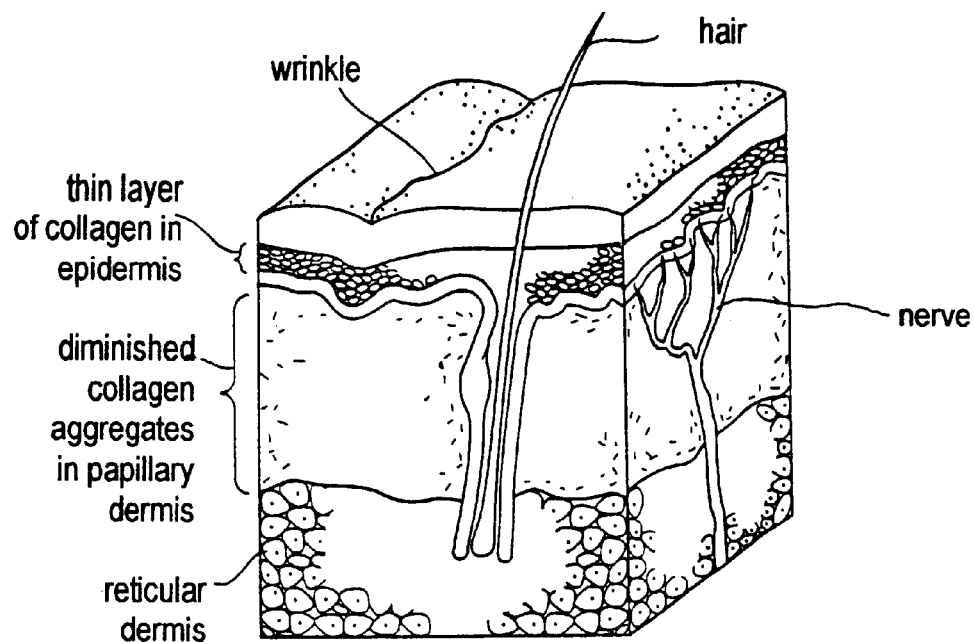
FIGS. 1A–1B are sectional illustrations of a patient's skin showing dermal layers.
Figure 1B:
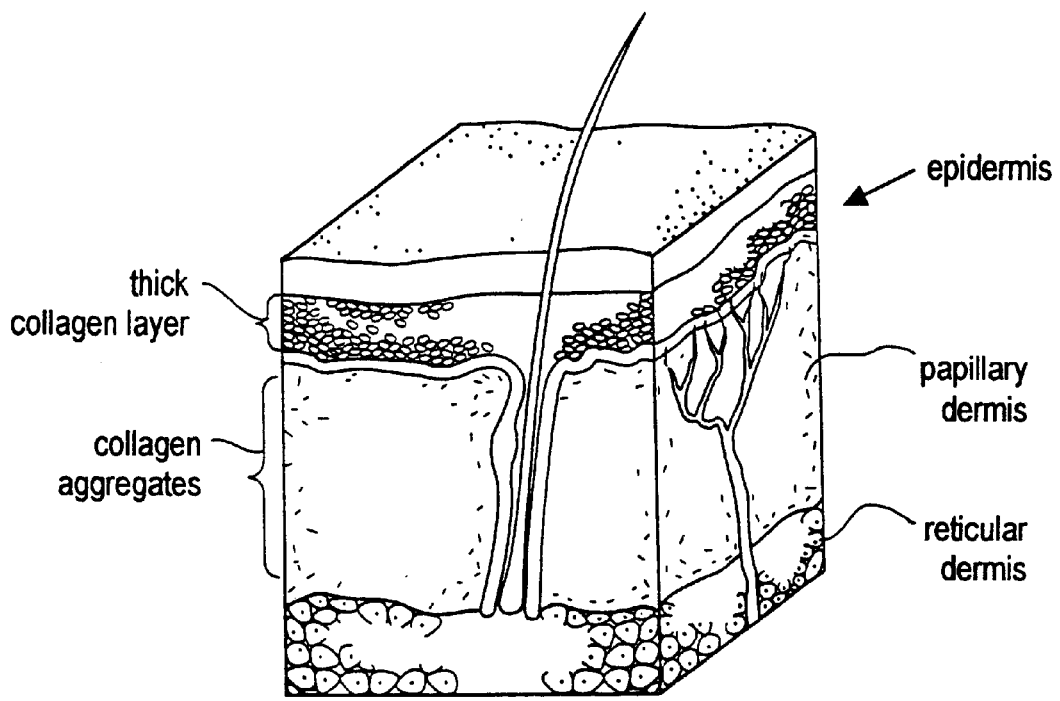
Figure 2A:
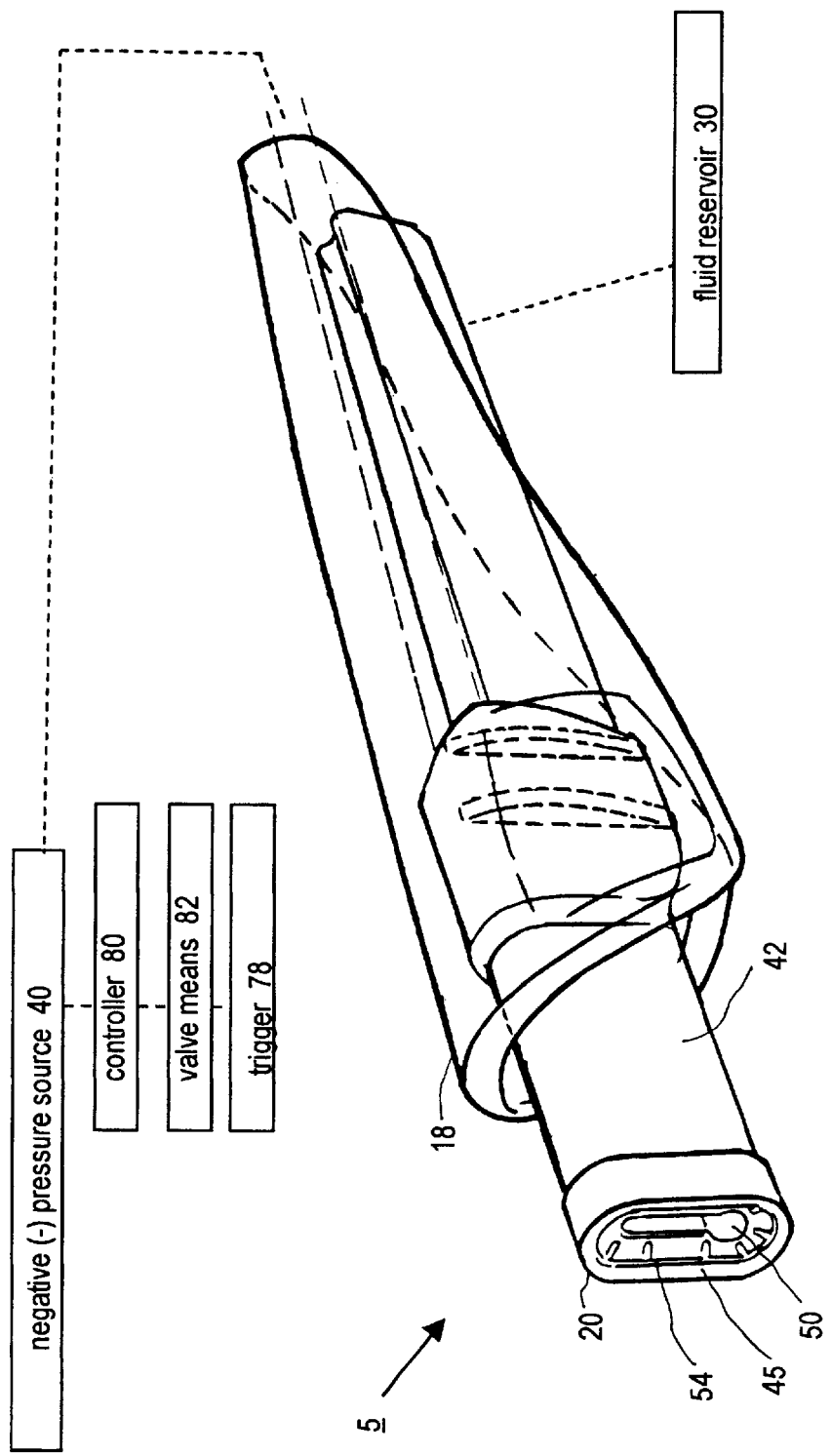
FIG. 2A is a perspective view of an exemplary Type "A" body and working end of the instrument of the invention.

1. Type "A" Skin Treatment System. FIGS. 2A–2B illustrate an exemplary instrument system 5 that is designed for atraumatic removal of skin layers in a skin resurfacing or rejuvenation treatment. This embodiment of instrument system 5 comprises (i) a hand-held instrument 18 with a removable working end portion 20; (ii) a fluid source or reservoir 30 for supplying fluids to the working end 20; and (iii) a negative (−) pressure source (or aspiration source) indicated at 40 that aspirates fluid and skin debris from a treatment site TS on the patient's skin.

FIG. 2A shows that the working end 20 is carried by, and preferably but optionally detachable from, an intermediate body section indicated at 42. This embodiment has fluid reservoir indicated at 30 that also is detachably coupled to body section 42. This instrument body 18 is adapted to use a detachable ergonomic handle portion 43 that has mating ribs 44a that cooperate with notches 44b in body section 42. In this preferred embodiment, the reservoir 30 carrying a fluid F is a disposable cartridge that may be fitted to body section 42 with a breakable seal 46 and male and female fittings 47a and 47b as are known in the art (see FIG. 2B). The working end 20 described below also is detachable, inexpensive and disposable.

Figure 3:
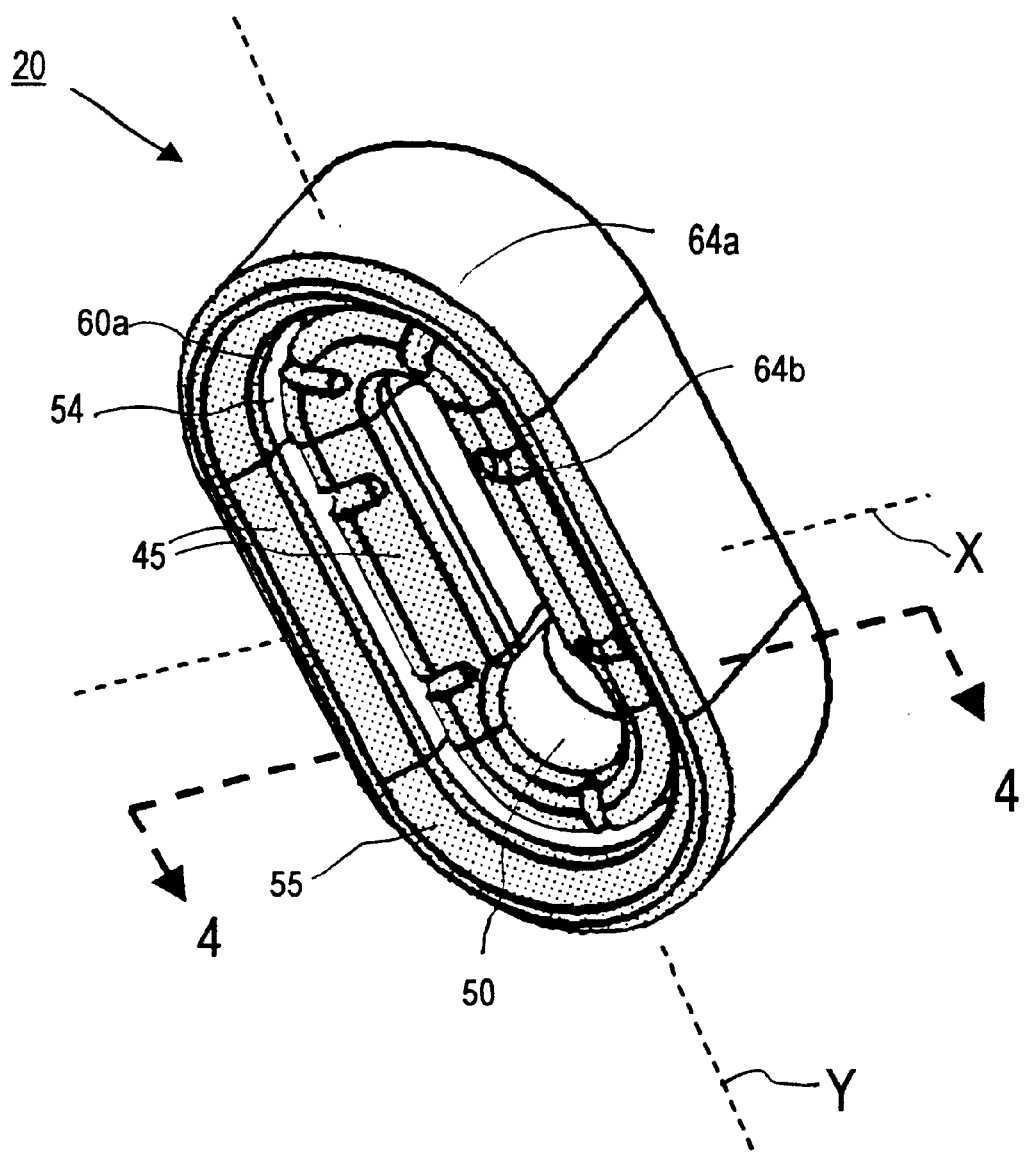
FIG. 3 is an enlarged perspective view of the working end of the instrument of FIGS. 2A–2B.

More in particular, referring to FIG. 3, the working end 20 defines a skin interface surface portion indicated at 45 that is adapted to engage the skin surfaces as the working end is translated across a patient's skin. In this embodiment, the skin interface 45 comprises the distal-facing surface region of the working end that is within the concave form 48 of working end 20. In this exemplary embodiment, the skin interface 45 transitions into an opening portion 50 generally centrally located in the working end. The opening 50 communicates with an interior passageway 51 that extends through body section 42 and further communicate with flexible tubing 52 that extends to the remote negative (−) pressure source 40 (see FIG. 2B). In this embodiment, there are a plurality of inflow apertures 54 generally about a perimeter of the skin interface that are in fluid communication with the fluid reservoir 30 as will be described further below.

Of particular interest, referring to FIG. 3, the skin interface 45 and optionally the entire working end 20 is formed of any suitable resilient material to allow the working end and skin interface 45 to flex and bend to atraumatically engage the skin surface as the working end is translated across a treatment site. It has been found that silicone is an ideal material that flexes desirably as described below in a method of the invention.

Figure 4:
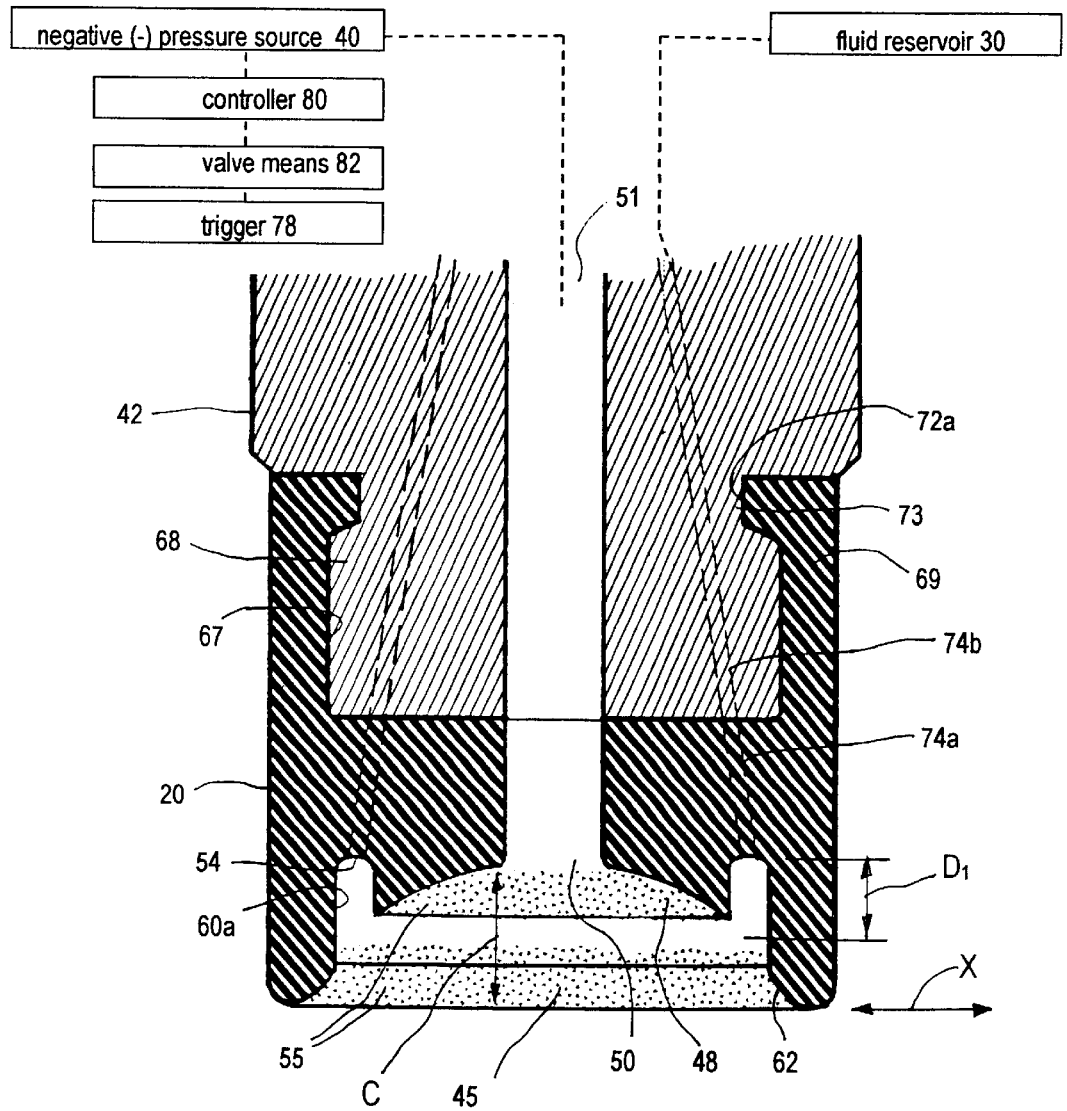
FIG. 4 is a sectional view of the exemplary working end of FIG. 3 taken along line 4—4 of FIG. 3.
Figure 5:
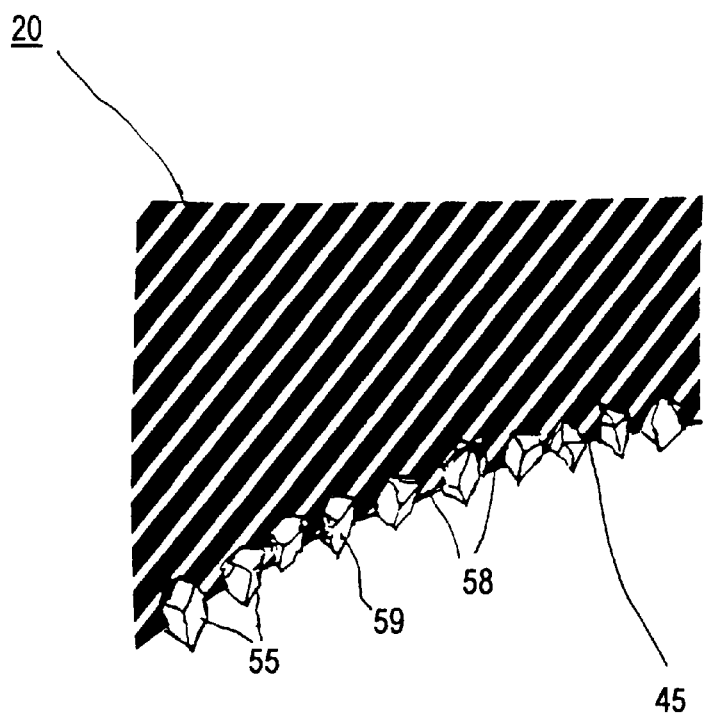
FIG. 5 is a greatly enlarged sectional view of a skin interface portion of the exemplary working end of FIG. 3 showing diamond particles carried therein taken along line 5—5 of FIG. 4.

Also of particular interest to the invention, referring to FIGS. 4 and 5, the skin interface 45 carries a diamond dust, fragment or particulate composition indicated at 55. A natural diamond fragment composition 55 has been found to have very sharp projecting points, edges and apices 57 that create an abrasive architecture that is well adapted to remove skin surface layers as the interface 45 carrying the diamond fragments is moved across a treatment site. Further, it has been found that spaces indicated at 58 between the diamond apices 57 will not tend to collect skin detritus when a fluid F (e.g., sterile water) generally flows across and about the skin interface 45 under the force of negative pressure from the aspiration source 40. It is believed that such removed skin particles or skin detritus do not adhere about the abrasive architecture of the skin interface 45 due to the fact that (i) the facets 59 of the diamond particles are very smooth and resist tissue adherence, and (ii) that the resilient material carrying the diamond fragments (e.g., silicone) is naturally lubricious and non-stick thus resisting any clogging of the spaces in the architecture of the skin interface 45. The ability of the fluid flow across the skin interface to remove skin detritus to the interior opening 50 for aspiration to a collection reservoir is very important for performing the method of the invention. As will be described below, the working end is passed over patient's skin in numerous paths, and the skin interface 45 must be continually free of detritus to allow a predictable level of skin surface removal during each portion of the working end's translation over a treatment site. It has been found that diamond fragments ranging in size from about 10 μm to 250 μm in maximum cross-sectional dimension may be used in the skin interface to remove tissue. The different sizes of fragments cause very different characteristics in skin surface removal, and it has been found that different skin types and different desired depths of skin surface removal can be optimized by using a selected size of diamond fragment. For a thin, sensitive skin and a thin layer removal, preferably, the diamond crystals are from about 10 μm to about 50 μm in maximum cross-sectional dimension. For a thicker skin, or oily skin, and for a deeper layer removal, preferably, the diamond crystals are from about 30 μm to about 100 μm in maximum cross-sectional dimension.

Since each range of dimensions of the diamond fragments produces a differing ability to cut skin surface layers, another feature of the invention is to provide color coding to different working ends 20 that carry different dimensions of diamond fragments. It is believed that three to six colors may be appropriate for different ranges of cutting ability. In this embodiment, the molded silicone of the skin interface can be colored. A preferred method has been developed for partially embedding the diamond fragments 55 in the skin interface which comprises distributing a very thin, dispersed layer of the fragments in an injection mold and thereafter introducing silicone into the mold. By using a selected viscosity of introduced silicone and a selected dispersion of the fragments in the mold, the silicone will form and set about the fragments 55 as generally indicated in FIG. 5.

As shown in FIGS. 3–4, in this embodiment, the skin interface 45 defines an x-axis (X) and a y-axis (Y) wherein the direction of movement of the working end across a treatment site is generally in a direction along the x-axis as the operator sweeps the skin interface over the treatment site. The skin interface 45 has an overall transverse or x-axis dimension is from about 5.0 mm. to about 40.0 mm. with a larger dimensioned end being adapted for treating a larger skin area (e.g., arms, back, legs and décolletage). A typical x-axis dimension is from about 5.0 mm. to 15.0 mm. for a skin treatment site area TS around a patient's face. The dimension across the y-axis of the skin interface 45 may also be from about 5.0 mm. to about 40.0 mm. with the relation between the y-axis and x-axis being from 1:1 to about 3:1. In a preferred embodiment, the ratio y-axis/x-axis ratio is from about 1:1 (as is a round working end) to about 2:1 as shown in the plan shape of FIG. 3 or in an oval plan shape. The surface area of the skin interface 45 (e.g., in mm.$^2$) about opening 50 may be from about 5.0 mm.$^2$ to about 100.0 mm.$^2$ to remove skin surface layers efficiently. It has been found that the shape of the concave form 48 of the working end is very important for the practice of the method and the depth C of the concavity may range from about 0.5 mm. to about 10.0 mm. depending on the overall dimensions across the working end (see FIG. 4).

Figure 6:
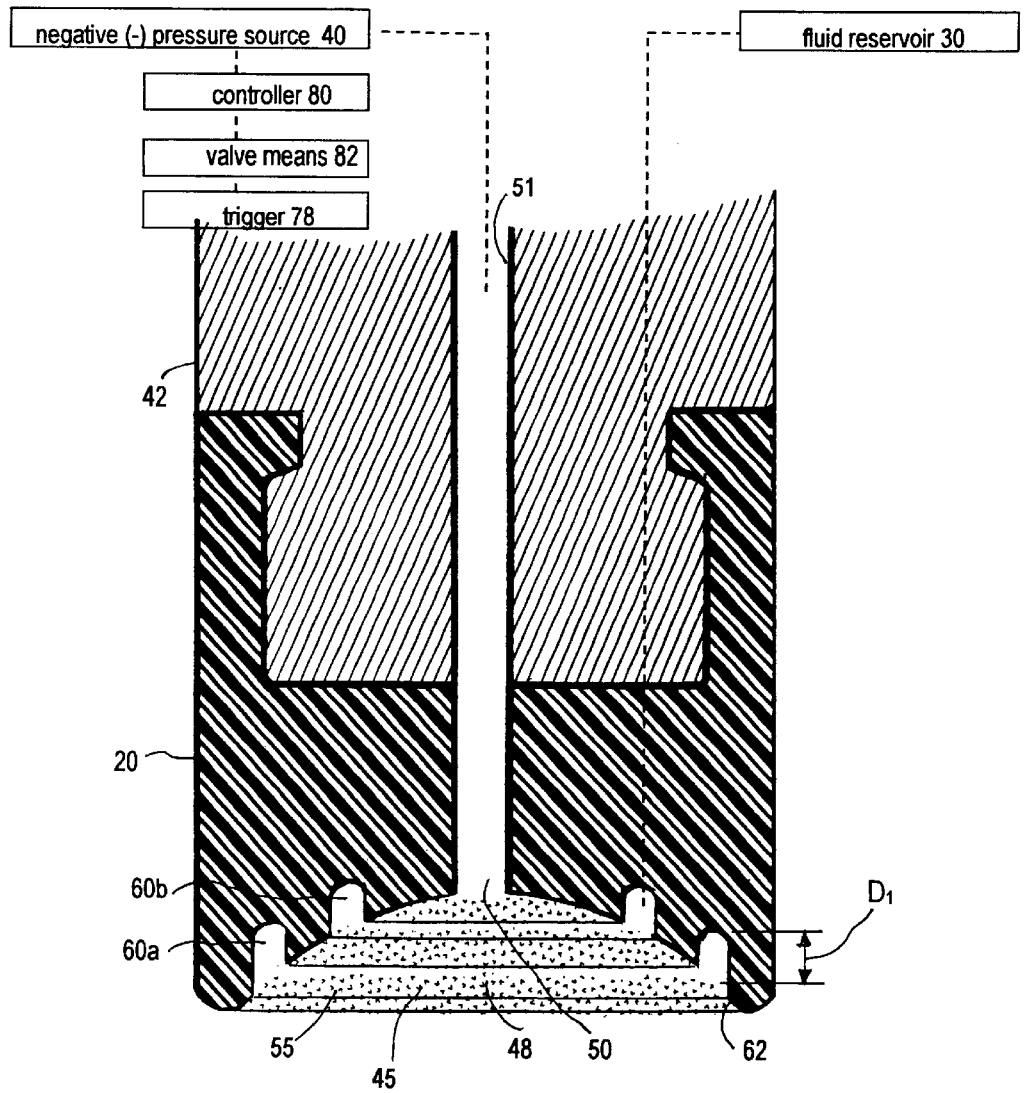
FIG. 6 is a sectional view of an alternative working end that is similar to the working end of FIG. 3.
Figure 7:
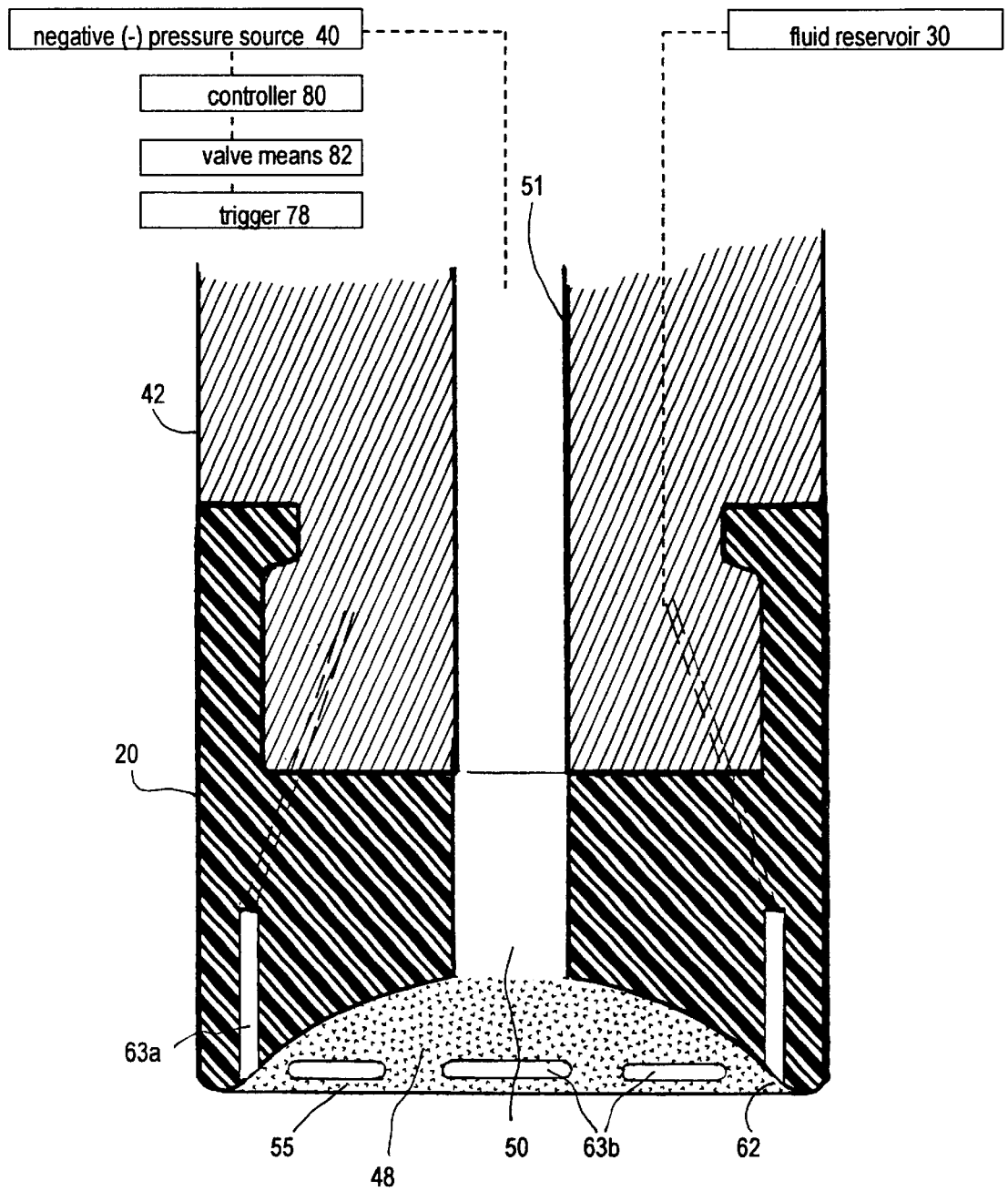
FIG. 7 is a sectional view of another alternative working end that is similar to the working end of FIG. 3.
Figure 8A:
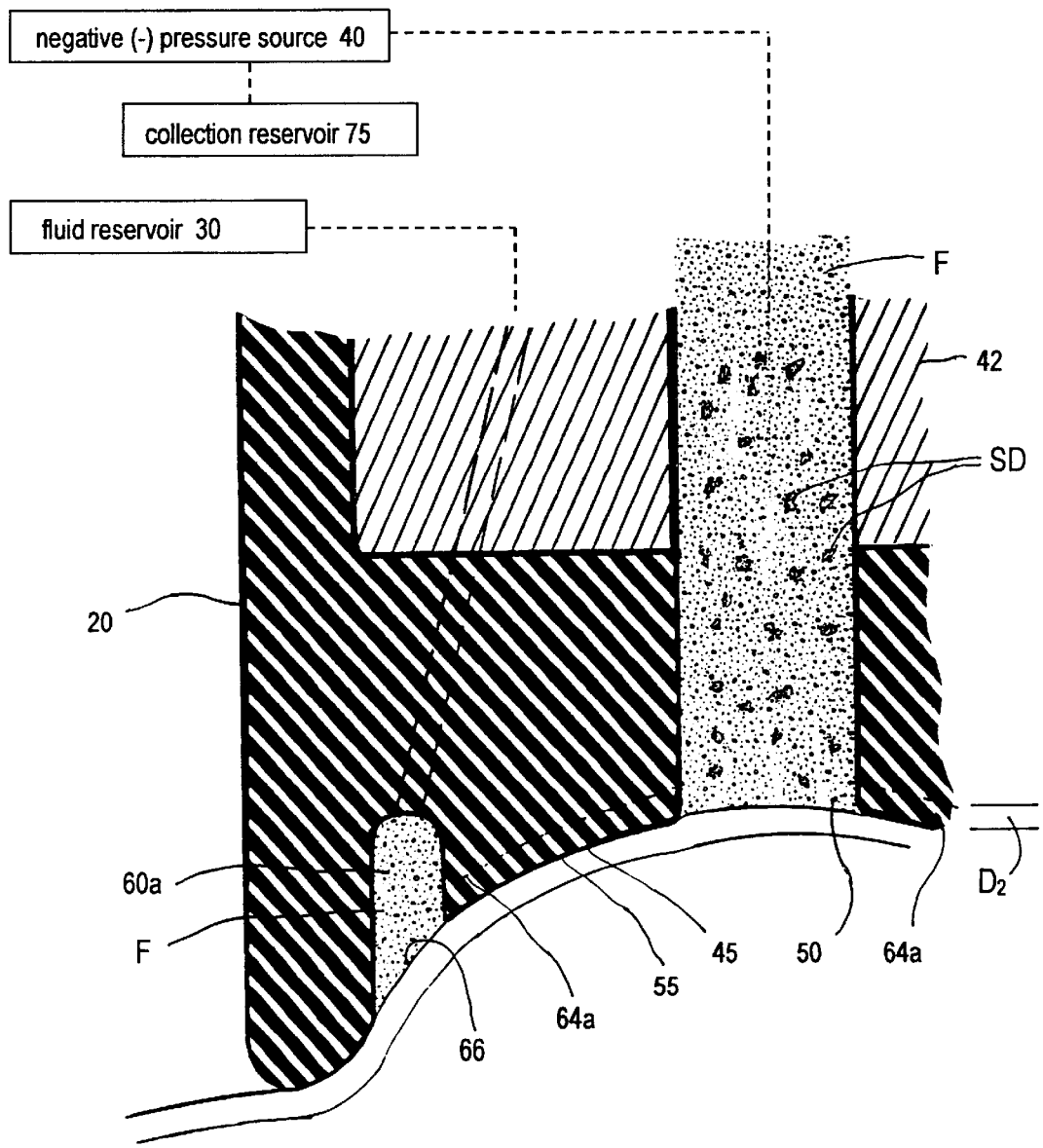
FIG. 8A is a greatly enlarged sectional view of a working end surface shown engaging a patient's skin in a method of the invention.
Figure 8B:
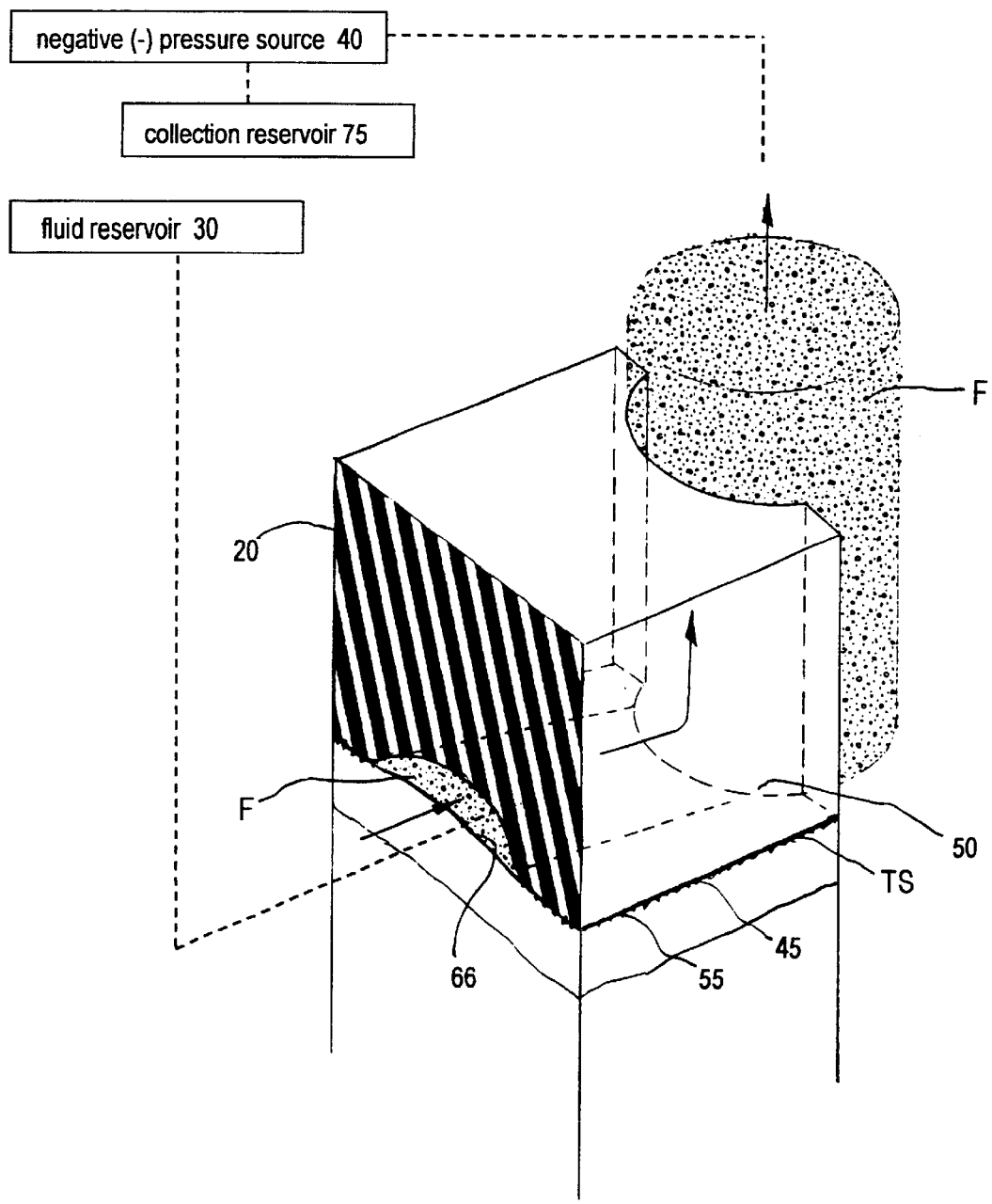
FIG. 8B is a sectional view of the working end surface of FIG. 9A showing a radial groove.
Figure 9:
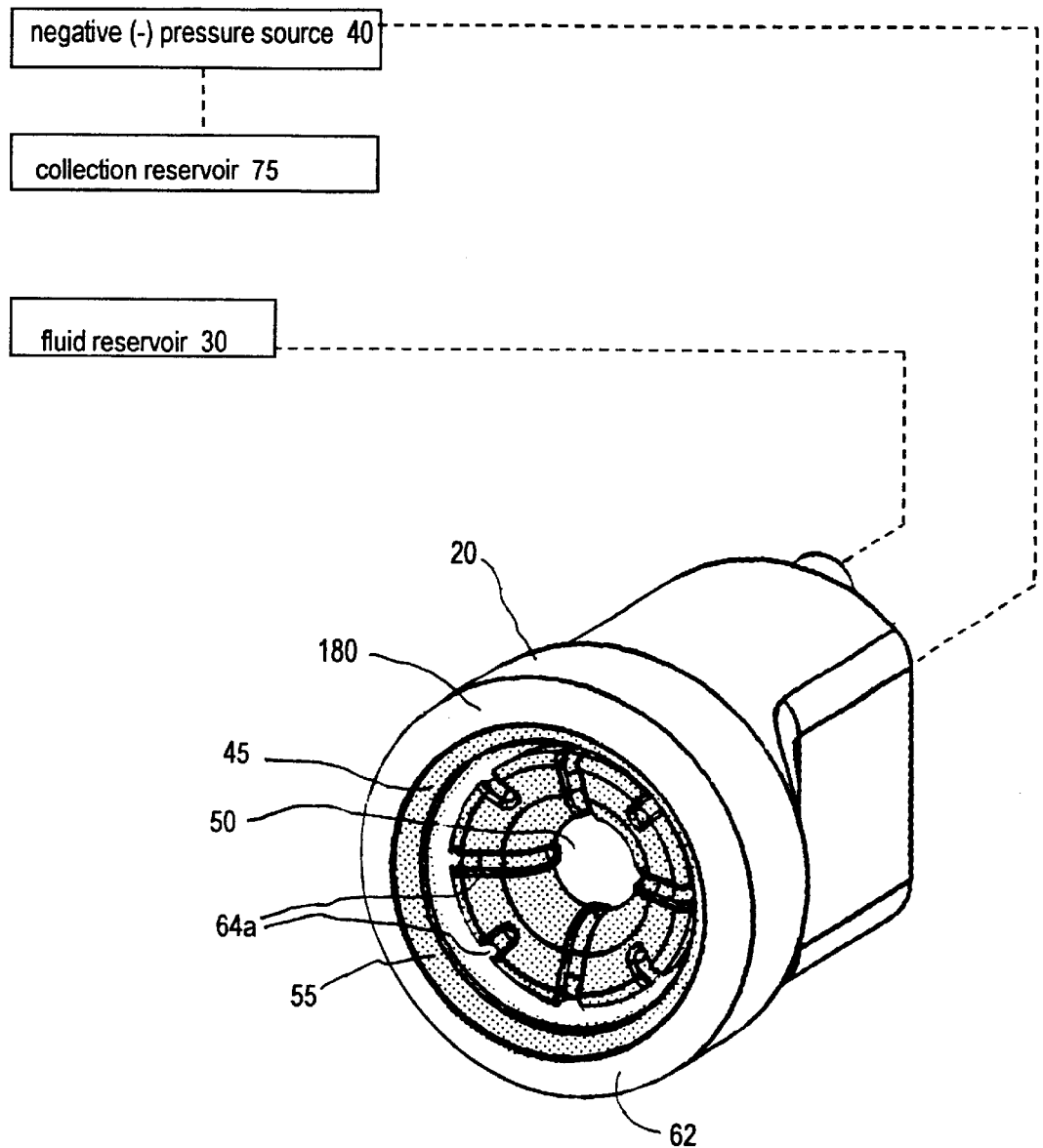
FIG. 9 is a perspective view of an alternative working end similar to that of FIG. 3 with an alternative plan shape.

As can be seen in FIGS. 3–4, in this embodiment, the fluid inflow apertures 54 are located in one or more generally circumferential recessed portions or grooves 60a–60n in the skin interface 45 generally around opening 50. As can be understood easily, the negative pressure source 40 will draw fluid F into the concave form 48 of the working end when a perimeter 62 of the working end is pressed against a skin surface. It is desirable to have a suitable flow of fluid F generally across the opposing sides of the skin interface and into opening 50. It has been found that recesses or grooves 60a–60n of a selected dimension desirably maintain a ready amount of fluid F therein as the skin interface is moved over the skin. FIG. 6 shows a slightly different embodiment configured with two recesses or grooves 60a and 60b. FIG. 7 shows another slightly different embodiment with a plurality of inflow apertures 63a about a perimeter 62 of the working end without any substantial recesses or grooves but the apertures widening at their open distal termination indicated at 63b. It should be appreciated that the working end may be configured with micro-porosities (not shown) about the skin interface to serve as fluid inflow apertures 54 and fall within the scope of the invention. The optional grooves 60a–60n shown in FIGS. 3–4 are deep enough (having dimension $D_1$ in FIGS. 4 & 8A) so that the skin surface 66 can not be drawn entirely into the recess thus allowing the recess to be maintained with fluid therein during a treatment. It also has been found that generally radial recessed portions 64a–64n are useful for directing the flow of fluid F toward opening 50. The radial recessed portions or grooves 64a–64n have a depth $D_2$ shown in FIGS. 8A–8B that is generally shallower than the depth of grooves 60a–60n. By the term radial, it is meant that the recessed portions may extend directly toward opening 50 or at an angle relative to opening 50 and collectively, some of such grooves will generally be angled relative to the direction of translation of the workin. As shown in FIG. 8B, it is believed that the skin surface 66 will be slightly pulled into a groove 64a as the skin interface moves across skin and the fluid F within and about the groove will assist in removing skin detritus SD from the treatment site and be aspirated into central opening 50. The radial recessed portions or grooves 64a–64n may extend partly toward to central recess and opening 50 as shown in FIG. 3 or entirely to the central opening as shown in the alternative working end embodiment of FIG. 9.

Referring again to FIG. 4, it can be seen that working end 20 is detachable from body 42 by means of a male and female fitting. Working end 20 has a female or recessed portion 67 that sealably mates with the projecting portion 68 of body portion 42. Since working end 20 is of resilient material, the wall portion 69 of the working end 20 can be stretched and lip portion 72a locks into annular groove 73 of the body 42 to form a fluid-tight seal. The opening 50 of the working end 20 is then in alignment with interior passageway 51 of body 42. Likewise, the apertures 54 transition into an system of interior fluid flow channels 74a in the working end 20 that align with similar channels 74b in body 42 that communicate with fluid reservoir 30.

In the exemplary system, the aspiration source 40 thus has multiple simultaneous functions: (i) to draw the skin surface into the concave form 48 of working end 20 and more particularly against the skin interface 45 and diamond abrasive architecture to perform the method of removing skin surface layers; (ii) to draw a fluid F across the skin interface 45 diamond abrasive architecture 55 to remove and clean skin debris from the skin interface; and (iii) to further aspirate the skin debris and fluid volume F to a remote collection reservoir 75. Besides these functions, it has been found that patients find the fluid F to have a desirable cooling and hydrating effect (when compared to prior art high-velocity air-driven particle skin abrasion methods). The aspiration source or negative (−) pressurization source 40 may be any suitable vacuum source known in the art. The reservoir 30 is vented as is known in the art. Between the aspiration source 40 and the remote collection reservoir 75 is a filter 76 subsystem that is known in the art for collecting aspirated skin debris and fluid. The collection reservoir 75 and filter 76 are preferably of inexpensive plastic and other materials that are disposable.

The aspiration source 40 is preferably provided with a controller 80 and adjustable valve means 82 for adjusting the pressure level setting to any suitable range. The system operator will learn from experience how to balance the pressure level to attain the desired level of suction against the patient's skin. A trigger or switch component 78 is provided as a foot-switch (FIG. 2A) but any suitable finger switch in body 18 also may be used.

2. Practice of the Method of the Invention. Turning again to FIGS. 8A–8B, a sectional view of working end 20 shows the technique of the present invention in abrasive removal of skin surface layers. FIG. 8A shows the working end 20 after actuation of the negative (−) pressure source 40 with the skin surface 66 initially being drawn into the concave form 48 of the working end. The operating negative pressures may be in any suitable range that is determined by investigation. The flexibility of the resilient material of the working end allows the perimeter 62 of the working end to flex slightly to conform to the skin surface. It has been found by experimentation that optimal pressure levels vary greatly depending on (i) the type of skin targeted for treatment, (ii) the dimensions across the working end, and (iii) the dimensions of opening 50.

Next, the operator moves the skin interface 45 across a treatment site TS which is a path on the patient's skin while still actuating the trigger 78 thereby maintaining the negative pressure environment in the concavity 48 and opening 50. The sideways or generally lateral movement of the skin interface 45 allows the diamond architecture 55 to abrade the surface layers. Referring to FIG. 8B, the shallow radial groove 64a generally has a flow of fluid F (in the direction of arrows) therethrough which carries skin debris SD and fluid F to the opening 50 for aspiration to the collection reservoir 75. The translation of the skin interface 45 over the treatment site TS allows an abrasion and removal of the skin surface in a controllable manner. p It has been discovered that patients find the skin surface removal techniques disclosed herein to be substantially painless for limited depth surface removal. It has further been found that deeper skin surface removed procedures with the resilient working end 20 is substantially pain-free, particularly when compared to prior at skin removal methods for a similar depth treatment. It is believed that an important novel aspect of the invention is the suspension of the diamond fragments 55 in a resilient substrate such as silicone. It is postulated that the slight movement or adjustment of individual diamond fragments 55 of the diamond abrasive architecture in the resilient substrate as the skin interface 45 is translated over skin allows the diamonds to float to a slight extend and cut the skin surface in an atraumatic manner.

The negative pressure environment within the working end causes the fluid F and skin debris SD to be entrained in an air volume to be drawn through passageway 51 to the collection reservoir 75. After translating the working end over a treatment site, the operator may release trigger 78 to easily lift the working end from the patient's skin or simply reverse the movement of the device. The treated path can be easily seen and the operator then can remove skin layers in another slightly overlapping or adjacent path by repeating the above steps until surface removal is completed over the targeted treatment area. Following a treatment, of preferably a series of treatments over time, new skin surface layers including increased collagen aggregation in the papillary dermis will occur to provide a rejuvenated skin texture.

Specific features of the invention may be shown in some figures and not in others, and this is for convenience only and any features may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A system for treating surface layers of a patient's skin, comprising:
    (a) an instrument body with a distal working end for engaging a skin surface;
    (b) a skin interface portion of the working end comprising an abrasive fragment composition secured thereto;
    (c) at least one inflow aperture in said skin interface in fluid communication with a fluid reservoir; and
    (d) at least one outflow aperture in said skin interface in communication with a negative pressurization source.

2. The system of claim 1 wherein the skin interface portion of the working end is formed of a resilient material.

3. The system of claim 1 wherein the abrasive composition comprises diamond fragments.

4. The system of claim 3 wherein the diamond fragments have a cross-sectional dimension ranging from about 10 microns to 250 microns.

5. The system of claim 1 wherein there are a plurality of inflow apertures located about a periphery of the skin interface portion.

6. The system of claim 1 wherein the at least one outflow aperture is located generally centrally in the skin interface portion.

7. The system of claim 1 wherein the skin interface is concave.

8. The system of claim 1 wherein the skin interface carries at least one groove structure for facilitating fluid flow thereacross.

9. The system of claim 1 wherein the plan shape of the skin interface portion is selected from the class of generally round, oval, and oblate.

10. A hand-held instrument for treating surface layers of a patient's skin, comprising:
    a skin interface portion of the hand-held instrument comprising an abrasive fragment composition secured thereto for abrading said surface layers;
    a fluid reservoir carried in said hand-held instrument; and
    at least one inflow aperture in said skin interface in communication with said fluid reservoir for carrying a fluid to said skin interface.

11. The system of claim 10 further comprising:
    at least one outflow aperture in said skin interface;
    a remote negative pressurization source in communication with said at least one outflow aperture for carrying fluids and abraded skin away from the skin.

12. A method for treating surface layers of a patient's skin, comprising:
    (a) providing an instrument with a distal working end having a skin interface surface portion having an exposed abrasive fragment architecture;
    (b) actuating a negative pressurization source in fluid communication with at least one aperture in said skin interface thereby drawing skin in contact with said abrasive fragment architecture;
    (c) translating said skin interface across a treatment site thereby cutting away a surface layer portion while maintaining negative pressurization between the skin interface and the skin; and
    (d) contemporaneous with step (c) flowing a fluid generally about the skin interface between at least one inflow and outflow aperture in said skin interface under the influence of the negative pressurization source.

13. The method of claim 12 wherein in step (d), the fluid flow removes skin debris from the treatment site.

14. The method of claim 12 wherein in step (d), the fluid flow hydrates the patient's skin.

15. The method of claim 12 wherein in steps (a) through (c) are repeated in a treatment period over a treatment site.

16. A working end of an instrument for treating surface layers of a patient's skin, comprising:
    a working end having a working surface with a concave form;
    said working surface of resilient material comprising an abrasive fragment composition partly embedded therein for cutting skin surface layers; and
    an arrangement of fluid inflow and outflow apertures in the working surface.

17. The working end of claim 16 further including a negative pressurization source in fluid communication with the outflow aperture.

18. The working end of claim 16 further including a fluid source in fluid communication with the inflow aperture.

19. The working end of claim 16 wherein the abrasive fragment composition comprises diamond fragments.

20. The working end of claim 16 wherein the abrasive fragment composition comprises sharp-edged fragments having a cross-sectional dimension ranging from about 10 microns to 250 microns.

21. An instrument for treating surface layers of a patient's skin comprising:

a body having a working end;

the working end having a suction port coupleable to a negative pressurization source, a fluid port coupleable to a fluid source, and a skin interface surface;

said skin interface surface comprising a skin-abrading surface;

whereby skin debris created by movement of said skin-abrading surface over the skin surface of a patient is removed from the skin surface along with fluid from the fluid source through the suction port.

22. The instrument according to claim 21 wherein the working end is a removable and replaceable working end.

23. The instrument according to claim 21 wherein the working end comprises an elastomeric working end body.

24. The instrument according to claim 21 wherein the working end comprises a working end body and the skin-abrading surface comprises abrasive particles embedded in the working end body.

25. The instrument according to claim 24 wherein said particles comprise diamond fragments.

26. The instrument according to claim 21 wherein the skin interface surface defines a working cavity, said suction port and said fluid port opening into said working cavity.

27. The instrument according to claim 26 further comprising a fluid distribution groove formed into said skin interface surface, said fluid port opening into said groove.

28. The instrument according to claim 26 further comprising a plurality of said fluid ports coupleable to a fluid source.

29. The instrument according to claim 21 further comprising a fluid source mountable to the body.

30. The instrument according to claim 29 wherein said fluid source comprises a liquid source.

31. An instrument system for treating surface layers of a patient's skin comprising:

the instrument according to claim 21;

a negative pressurization source and a fluid source coupled to the instrument.

32. An instrument for treating surface layers of a patient's skin comprising:

a body having a removable and replaceable working end;

a liquid source mountable to the body;

the working end comprising a working end body, the working end body comprising a suction port coupleable to a negative pressurization source, a fluid port coupled to the liquid source, and a skin interface surface;

said skin interface surface comprising a skin-abrading surface with abrasive particles embedded therein; and the skin interface surface defining a working cavity, said suction port and said fluid port opening into said working cavity;

whereby skin debris created by movement of said skin-abrading surface over the skin surface of a patient is removed from the skin surface along with fluid from the fluid source through the suction port.

33. A replacement working end for a skin surface treatment instrument of the type comprising a body coupleable to a negative pressurization source and a fluid source, the replacement working end comprising:

an elastomeric body portion comprising a skin interface surface, a suction port, a fluid port, and a skin interface surface;

the skin interface surface comprising a skin-abrading surface;

the skin interface surface defining a working cavity, said suction port and said fluid port opening into said working cavity so that skin debris created by movement of the skin-abrading surface over the skin surface of a patient is removed from the skin surface along with fluid from the fluid source through the suction port.

34. The replacement working end according to claim 33 wherein said elastomeric body portion constitutes the replacement working end.

35. The replacement working end according to claim 33 wherein the skin-abrading surface comprises abrasive particles partially embedded in at least a portion of the skin interface surface.

36. A method for treating the skin surface of a patient comprising:

placing a skin interface surface of a working end of a skin treatment instrument against the skin surface of a patient, the skin interface surface comprising a skin-abrading surface and defining a working cavity;

supplying a fluid to the working cavity;

abrading the skin surface by moving the skin-abrading surface over the skin thereby creating skin debris; and removing at least a portion of the fluid and the skin debris from the working cavity using a negative pressurization source coupled to the working cavity.

37. The method according to claim 36 wherein coupling the working cavity to the negative pressurization source causes the skin surface to be drawn against the skin-abrading surface.

38. The method according to claim 36 wherein the fluid supplying step is carried out using water as the fluid.

* * * * *